US008846205B2

(12) United States Patent
Keen et al.

(10) Patent No.: US 8,846,205 B2
(45) Date of Patent: Sep. 30, 2014

(54) HYBRID STRATEGIES FOR REDUCING LEACHING OF METAL BIOCIDES FROM BIODEGRADABLE SUBSTRATES

(75) Inventors: Brian T. Keen, Pinch, WV (US); Kimberly S. Hayson, Redhouse, WV (US); William C. Hoffman, Dunbar, WV (US); Albert F. Joseph, Charleston, WV (US)

(73) Assignee: Union Carbide Chemicals & Plastics Technology LLC

( * ) Notice: Subject to any disclaimer, the term of this patent is extended or adjusted under 35 U.S.C. 154(b) by 522 days.

(21) Appl. No.: 12/381,460

(22) Filed: Mar. 12, 2009

(65) Prior Publication Data

US 2009/0258943 A1 Oct. 15, 2009

Related U.S. Application Data

(60) Provisional application No. 61/069,484, filed on Mar. 14, 2008.

(51) Int. Cl.
*A01N 59/20* (2006.01)
*B27K 3/16* (2006.01)
*B27K 3/50* (2006.01)

(52) U.S. Cl.
CPC . *A01N 59/20* (2013.01); *B27K 3/50* (2013.01); *B27K 3/16* (2013.01)
USPC .......................................................... 428/541

(58) Field of Classification Search
USPC .......................................................... 428/541
See application file for complete search history.

(56) References Cited

U.S. PATENT DOCUMENTS

| | | |
|---|---|---|
| 4,567,115 A | 1/1986 | Trumble |
| 4,847,002 A | 7/1989 | Trumble et al. |
| 4,929,454 A | 5/1990 | Findlay et al. |
| 5,304,237 A | 4/1994 | Barth et al. |
| 5,342,438 A | 8/1994 | West |
| 5,395,656 A | 3/1995 | Liang |
| 5,460,751 A | 10/1995 | Ma et al. |
| 5,635,217 A | 6/1997 | Goettsche et al. |
| 5,846,305 A | 12/1998 | Payzant |
| 5,853,766 A | 12/1998 | Goettsche et al. |
| 5,874,025 A | 2/1999 | Heuer et al. |
| 6,110,263 A | 8/2000 | Goettsche et al. |
| 6,395,698 B1 | 5/2002 | Daun et al. |
| 6,428,902 B1 | 8/2002 | Amundson et al. |
| 6,489,037 B1 | 12/2002 | Winterowd et al. |
| 2003/0077219 A1 | 4/2003 | Ploss et al. |
| 2004/0258767 A1 | 12/2004 | Leach et al. |
| 2004/0258768 A1 | 12/2004 | Richardson et al. |
| 2004/0258838 A1 | 12/2004 | Richardson et al. |
| 2005/0118280 A1 | 6/2005 | Leach et al. |
| 2005/0249812 A1 | 11/2005 | Leach et al. |
| 2005/0256026 A1 | 11/2005 | Hodge et al. |
| 2005/0265893 A1 | 12/2005 | Leach et al. |
| 2006/0078686 A1 | 4/2006 | Hodge et al. |
| 2006/0086284 A1 | 4/2006 | Zhang et al. |
| 2006/0112850 A1 | 6/2006 | Zhang et al. |
| 2006/0147632 A1 | 7/2006 | Zhang et al. |
| 2006/0162611 A1 | 7/2006 | Richardson et al. |
| 2010/0016426 A1 | 1/2010 | Hayson et al. |

FOREIGN PATENT DOCUMENTS

| | | |
|---|---|---|
| AU | B-15517/92 | 10/1992 |
| EP | 0381482 A2 | 8/1990 |
| EP | 0514644 | 11/1992 |
| EP | 0641633 | 3/1995 |
| EP | 0739698 | 4/1995 |
| EP | 0682091 | 11/1995 |
| EP | 0747182 | 12/1996 |
| WO | WO 98/39146 | 9/1998 |
| WO | WO 02/47876 | 6/2002 |
| WO | WO 2004/011215 | 2/2004 |
| WO | WO 2005007368 | 1/2005 |
| WO | WO 2006044225 | 4/2006 |
| WO | WO 2006053284 | 5/2006 |
| WO | WO 2006/065684 | 6/2006 |
| WO | WO 2006/072659 | 7/2006 |
| WO | WO 2007/133220 | 11/2007 |
| WO | WO 2008/013981 | 1/2008 |
| WO | WO 2009/078945 A2 | 6/2009 |

OTHER PUBLICATIONS

MSDS for ACQ-1.*
Townsend TG and Solo-Gabriele H, "Environmental Impacts of Treated Wood" Taylor & Francis Group, Boca Raton, 2006.*
Heaton et al., "Studies on biocide release and performance of novel anti-fungal paints," 1991, Biofouling: The Journal of Bioadhesion and Biofilm Research, vol. 3, Issue 1, pp. 35-43 (Abstract only available; attached).

* cited by examiner

Primary Examiner — Paul Zarek
(74) Attorney, Agent, or Firm — Kagan Binder, PLLC

(57) ABSTRACT

Hybrid strategies generally involve treating biodegradable substrates with preservative compositions having at least two phases in which the metal biocide is distributed among at least the two phases and via equilibrium reactions moves between the two phases. Both phases are caused to contact the substrate in a manner so that the phases are in contact with each other during at least a portion of the treatment. In illustrative embodiments, the first phase is a liquid phase comprising complexed metal biocide dissolved in a liquid carrier, while the second phase comprises particles comprising the metal biocide, often precipitated and/or colloidal particles. The strategies and related compositions, processes, and treatments are hybrid in the sense that the strategies include both heterogeneous (insoluble) and homogeneous metal biocide constituents. Unlike heterogeneous strategies, hybrid strategies are less sensitive to particle size constraints and may use biocide particles with a wider range of particle sizes. Unlike homogeneous strategies, hybrid strategies are less sensitive to pH and may use a wider range of complexing agents, including mildly alkaline amines such as triethanolamine.

28 Claims, No Drawings

HYBRID STRATEGIES FOR REDUCING LEACHING OF METAL BIOCIDES FROM BIODEGRADABLE SUBSTRATES

PRIORITY

The present non-provisional patent application claims benefit from U.S. Provisional Patent Application having Ser. No. 61/069,484, filed on Mar. 14, 2008, by Keen et al. and titled HYBRID STRATEGIES FOR REDUCING LEACHING OF METAL BIOCIDES FROM BIODEGRADABLE SUBSTRATES, wherein the entirety of said provisional patent application is incorporated herein by reference for all purposes.

FIELD OF THE INVENTION

The present invention relates to metal biocide-containing preservative compositions useful for protecting substrates such as wood, other cellulosic products, starch-based products, and the like that are vulnerable to decay due to insects, fungi, microbes, and the like, wherein at least one metal biocide constituent is present in both a soluble and insoluble form. The compositions have more resistance against leaching than if the entirety of the composition were to include soluble metal while also achieving much more thorough and uniform penetration into biodegradable substrates than if the composition were to include only insoluble metal. Thus, advantages associated with both heterogeneous and homogeneous compositions are obtained to a large degree while key drawbacks of using heterogeneous and homogeneous compositions individually are dramatically reduced.

BACKGROUND OF THE INVENTION

Substrates such as wood, starch-based, and other biodegradable products used in interior or exterior applications can be vulnerable to attack by insects, fungi, microbes, and the like. To prevent decay that tends to result from these attacks, such substrates may be treated with preservatives to protect against decay and increase longevity. Historically, one widely used preservative composition is known by the CCA designation. This designation stands for chromated copper arsenate. CCA compositions were widely used to treat wood products, e.g., Southern Yellow Pine, used for decks, fencing, landscape timbers, and the like.

CCA compositions provide excellent protection against decay. However, relatively recently, health and safety concerns have been raised concerning the arsenic and chromium content of these compositions. Consequently, regulatory guidelines caused CCA usage for residential applications to stop on Jan. 1, 2004. As a result, the industry has developed and continues to develop new preservatives as substitutes for CCA compositions. Uncovering effective substitutes that are chromium and arsenic free has been challenging.

One newer class of copper-based preservatives uses a form of complexed copper that is water-soluble. The resultant solutions are considered homogeneous in the sense that the solutions are a single, liquid phase as applied to substrates. In many embodiments, the copper is complexed with complexing agents such as an alkanolamine. Examples of preservatives that contain copper complexes include copper polyaspartic acid, alkaline copper quaternary ammonium salt (also referred to in the industry by terminology such as "alkaline copper quat" or "ACQ"), copper azole, copper boron azole, ammoniacal copper citrate, copper bis(dimethyldithiocarbamate), and copper ethanolamine carbonate. Commonly, all these have a nitrogen base that complexes copper and carbonate ions to stabilize the resultant complex. Preservative compositions incorporating copper complexed with alkanolamine are referred to by the designation copper-amine and currently dominate the preservative market for residential lumber applications.

As a positive, homogeneous preservative solutions tend to uniformly and thoroughly penetrate substrates. Unfortunately, as compared to biodegradable products treated with CCA materials, biodegradable products treated with these newer copper complex-based materials suffer higher copper losses in the field. Due to the water solubility of the complexes, the copper tends to leach more readily from the treated biodegradable products when exposed to rain or other water. The expectation that copper losses will occur due to leaching causes treatments to be made with larger amounts of copper to accommodate these expected losses. This is costly and wasteful. Also, copper solutions tend to be relatively sensitive to pH changes inasmuch as the soluble complexes can precipitate if the pH is too low. This limits formulation flexibility to the use of only alkaline complexing agents, for instance.

Heterogeneous preservative compositions also have been recently developed. In these, the metal biocide has been present in insoluble, particulate form dispersed in a liquid carrier. This dispersion, emulsion, or the like is then used to treat biodegradable substrates. Examples of heterogeneous preservative compositions in the form of dispersions of micronized copper containing particles are described, for example, in U.S. Pat. Publication Nos. 2004/0258767; 2005/0118280; 2005/0249812; 2005/0265893; 2006/0086284; 2006/0112850; and 2006/0147632.

As a positive, the copper containing particles in heterogeneous treatment compositions exhibit excellent retention characteristics and are highly resistant to leaching as compared to soluble, complexed copper. Unfortunately, the insoluble particles tend to reside only in the pores or other interstitial vacancies of substrates and penetrate poorly into cells or the like. This is believed to result in much less bioefficacy than could be obtained by more thorough and uniform substrate penetration. Heterogeneous strategies also suffer from particle size constraints, inasmuch as the effectiveness of the treatment can be compromised if the particles are too large or too small.

Thus, neither heterogeneous or homogeneous treatment strategies are wholly satisfactory. Homogeneous strategies have good bioefficacy, at least initially, but tend to leach too much. Heterogeneous strategies have good retention, but tend to have less bioefficacy than is desired. Some strategies that can achieve these benefits to a greater degree with lesser suffering from the drawbacks would be very desirable.

SUMMARY OF THE INVENTION

The present invention is based, at least in part, upon hybrid preservative strategies. The hybrid strategies of the present invention generally involve treating biodegradable substrates with preservative compositions having at least two phases. The metal biocide is distributed among at least the two phases and via equilibrium reactions moves between the two phases. Both phases are caused to contact the substrate in a manner so that the phases are in contact with each other during at least a portion of the treatment. In illustrative embodiments, the first phase is a liquid phase comprising complexed metal biocide dissolved in a liquid carrier, while the second phase comprises particles comprising the metal biocide, often precipitated and/or dispersed particles (e.g., colloidal particles are an illustrative kind of dispersed particles). The particles in the separate, second phase may be solid, liquid, and/or gel. If desired, the particles can be constituents of a latex, an emulsion, and/or the like. The strategies and related compositions, processes, and treatments are hybrid in the sense that the strategies include both heterogeneous (insoluble) and homogeneous metal biocide constituents.

Significantly, the present invention provides preservative treatment strategies that achieve the benefits of both heterogeneous and homogeneous strategies to a great extent while minimizing the drawbacks of each. That is, preservative treatment strategies of the invention allow more thorough and uniform substrate penetration than can be achieved using heterogeneous compositions alone while also showing much greater substrate retention characteristics than using homogeneous solutions alone. Unlike heterogeneous strategies, hybrid strategies are less sensitive to particle size constraints and may use biocide particles with a wider range of particle sizes. Unlike homogeneous strategies, hybrid strategies are less sensitive to pH and may use a wider range of complexing agents and other ingredients, including mildly alkaline amines such as triethanolamine.

In one aspect, the present invention relates to a preservative composition for treating biodegradable substrates. The composition comprises first and second phases, wherein at least a first portion of the metal biocide is incorporated into the first phase, wherein at least a second portion of the metal biocide is incorporated into the second phase, and wherein at least a portion of the metal biocide in the first phase is in equilibrium with at least a portion of the metal biocide in the second phase. The present invention also relates to using this preservative composition to treat a substrate. The treatment is carried out at least in part by causing the composition to contact the substrate.

In another aspect, the present invention relates to an aqueous preservative composition for treating biodegradable substrates. The composition is derived from ingredients comprising an aqueous liquid carrier, at least one metal biocide and at least one complexing agent, said at least one complexing agent being present in a stoichiometric deficiency relative to the at least one metal biocide under conditions such that a portion of the metal biocide is incorporated into a metal complex dissolved in the liquid carrier and at least a portion of the metal biocide is incorporated into a separate phase from the liquid carrier. The present invention also relates to using this preservative composition to treat a substrate. The treatment is carried out at least in part by causing the composition to contact the substrate.

In another aspect, the present invention relates to a method of making a preservative composition, comprising the steps of:
providing a homogeneous solution comprising a complexed metal biocide derived from ingredients comprising a metal biocide and a complexing agent; and
adding a sufficient amount of additional material comprising a metal biocide under conditions effective to form an admixture comprising two phases wherein a first liquid phase comprises complexed metal biocide and at least an additional portion of the metal biocide is incorporated into a second phase. In another aspect, the present invention relates to a method of preserving a biodegradable substrate, comprising the step of causing a preservative composition prepared in accordance with this method to contact the substrate.

In another aspect, the present invention relates to a method of making a preservative composition, comprising the steps of:
providing a heterogeneous composition comprising a metal biocide in a solid phase; and
causing a stoichiometric deficiency of a complexing agent relative to the metal biocide to be present in the composition under conditions to yield two phases, wherein a first liquid phase comprises complexed metal biocide and at least an additional portion of the metal biocide is incorporated into a second phase. In another aspect, the present invention relates to a method of preserving a biodegradable substrate, comprising the step of causing a preservative composition prepared in accordance with this method to contact the substrate.

In another aspect, the present invention relates to a method of making a preservative composition, comprising the steps of:
providing a heterogeneous composition comprising a metal biocide in a solid phase;
providing a homogeneous solution comprising a complex of a metal biocide; and
combining amounts of the composition and solution to form an admixture such that the admixture includes a solid phase comprising metal biocide and a soluble phase comprising metal biocide, said phases being in equilibrium. In another aspect, the present invention relates to a method of preserving a biodegradable substrate, comprising the step of causing a preservative composition prepared in accordance with this method to contact the substrate.

DETAILED DESCRIPTION OF PRESENTLY PREFERRED EMBODIMENTS

The embodiments of the present invention described below are not intended to be exhaustive or to limit the invention to the precise forms disclosed in the following detailed description. Rather the embodiments are chosen and described so that others skilled in the art may appreciate and understand the principles and practices of the present invention.

In many representative embodiments, a hybrid treatment strategy involves contacting the substrate with a fluid composition that is derived from ingredients including at least a liquid carrier comprising one or more constituents, at least one complexing agent, and at least one source comprising a metal biocide reactive with the complexing agent(s), wherein the complexing agent(s) is/are present in a deficiency relative to the metal biocide such that only a portion of the metal biocide is complexed so as to be dissolved in the liquid carrier. At least a portion of the excess metal biocide that is not complexed will exist in a separate phase from the liquid carrier. As used herein, such a deficiency of the complexing agent relative to the metal biocide will be referred to as a "stoichiometric deficiency" to indicate that there is only enough complexing agent(s) present to complex a portion of the metal biocide that is present. The ingredients are combined under conditions effective to provide such a two phase admixture in which a first, liquid phase comprises complexed metal biocide dissolved in the liquid carrier, and at least a portion of the excess metal biocide is incorporated into a second, separate phase, often as a constituent of precipitated and/or dispersed particles. The complexing agent is selected so that at least a portion of the complexed metal biocide in the first phase is in equilibrium with at least a portion of the metal biocide in the second phase. Consequently, due to equilibrium effects, metal biocide will transfer between/among phases over time. The hybrid composition may be prepared first and then used to carry out the treatment, or the hybrid composition may be formed in situ from two or more component compositions applied to the substrate simultaneously, sequentially, in overlapping fashion, or the like.

As compared to treatments using only heterogeneous metal biocide compositions, the hybrid approach leads to more thorough and more uniform penetration into the volume of the substrate than if all of the metal biocide were to be in an insoluble form in the first instance. As compared to treatments using identical total amounts of only homogeneous metal biocide compositions, hybrid biocide compositions demonstrate better retention (e.g., reduced leaching) in the substrate than if all of the metal biocide were to have been in a soluble form in the first instance. At least in part, this improved retention may be attributable to the factor that a significant portion of the metal biocide of a hybrid composition of the invention exists in an insoluble, more fixed state (e.g., particles) at any one time. Yet, as demonstrated in the Examples below, the retention of metal biocide is even better than would be expected from the relative proportions of the insoluble and soluble material. Consequently, the hybrid approach provides synergistic retention protection as well.

In short, hybrid strategies benefit from the fixed, impressive retention characteristics of heterogeneous preservative compositions and yet penetrate into substrates with much of the tenacity of homogeneous compositions. The benefits of each of the homogeneous and heterogenous systems are displayed to a large degree while the drawbacks (poor penetration and excessive leaching) are dramatically reduced. Significantly, the improved penetration of the metal biocide into the substrate is achieved without requiring all of the metal to be dissolved in the liquid carrier. The improved penetration is believed to provide better bioefficacy, better metal biocide retention, and longer lasting efficacy than treatments that yield lesser penetration.

Significantly, the use of hybrid formulations also allows formulations to be less pH sensitive. Hence, formulations can be formulated over a wider range of pH values, include much lower pH values than are typically more suitable for homogeneous solutions. This means that hybrid formulations can be formulated in illustrative embodiments at less alkaline pH values, e.g., from about 7 to about 8.5. Normally, copper species would be expected to precipitate from otherwise homogeneous solutions of complexed copper if the pH were to be too low, for example, but precipitation is not an issue for hybrid formulations where the presence of a precipitate is desired.

A wider range of ingredients can also be used in formulations that might not be as readily used at more alkaline pH values. For example, triethanolamine (TEA) is a mild base that is a common shampoo and cosmetic ingredient. TEA is a useful complexing agent in the practice of the invention in those embodiments formulated at lower pH values, e.g., less than about 9.0 or even less than about 8.5. TEA is less suitable in more alkaline formulations such as when the pH is greater than about 10.0 or higher.

As another example, being able to formulate at lower pH values such as below about 8.5 would allow more efficient use of pH-sensitive biocides such as the moldicides available from Rohm and Haas Co. under the KATHON trade designations. The KATHON moldicides have been widely used in the industry. A particularly preferred example of such a moldicide is available under the trade designation KATHON WT. This particular product is a mixture that includes about 3 parts by weight of 5-chloro-2-methyl-3-isothiazolinone and about 1 part by weight of 2-methyl-3-isothiazolinone. These moldicides generally are quite stable in the acidic CCA formulations, but can be prone to degradation when used in ACQ or similar alkaline formulations with pH values of over 8.5. Consequently, notwithstanding the expensive nature of the KATHON or similar moldicides, ACQ formulators have tended to use relatively larger amounts (e.g., about double the amount used in CCA formulations) of such moldicides in alkaline preservative compositions to account for degradation losses. Being able to formulate hybrid compositions of the present invention at less alkaline pH values is more efficient because degradation losses are reduced. Advantageously, this would allow lesser amounts of the expensive moldicide ingredients to be used.

Very significantly, hybrid formulations are much more independent of particle size constraints as compared to heterogeneous formulations, particularly with respect to the size of the insoluble material at the time of the initial treatment. As described in U.S. Pat. Publication Nos. 2004/0258767; 2005/0118280; 2005/0249812; 2005/0265893; 2006/0086284; 2006/0112850; and 2006/0147632, the micronized copper particles of conventional heterogenous formulations must not be too large or too small. If too large, the particles will not be able to get into the finer pores of wood substrates. Yet, if too small, the particles will be too prone to leaching. In contrast, the insoluble particles of the hybrid formulations of the present invention not only can be provided with size characteristics as recommended for conventional heterogeneous compositions, but also may be provided as much more coarse, or even more fine particles if desired. As discussed above, the characteristics of the hybrid formulation, believed to be attributable to equilibria effects among soluble and insoluble phases, help to assure more thorough and more uniform penetration of metal biocide supplied as insoluble particles.

The ability of the present invention to use starting materials comprising relatively coarse chunks of insoluble material was demonstrated in an experiment. Under a microscope, large coarse chunks of copper basic carbonate particles, larger than the size limit specified in U.S. Pat. Publication Nos. 2004/0258767; 2005/0118280; 2005/0249812; 2005/0265893; 2006/0086284; 2006/0112850; and 2006/0147632, were observed as chunks on the surface of a wood substrate. The surface was dry. Drops of a solution containing complexed copper were applied to the chunks by pipet. In a relatively short time, the chunks were entirely gone. The chunks were noticeably smaller after only about 30 minutes. The chunks were gone no more than after 24 hours. The hue in the region changed indicating that the heterogeneous chunks had been mobilized and penetrated into the substrate along with the homogeneous solution deposited by pipet.

Even when initially supplied in a relatively coarse form, the insoluble material becomes distributed within the substrate in a much more finely divided form. Again, it is believed that equilibria effects firstly dissolve the material as very finely sized, complexed metal. When equilibrium results in precipitation, the resulting precipitated material tends to be very finely divided, even more fine than would result by many physical grinding methods.

In sum, conventional, heterogeneous treatment compositions are limited by physical distribution mechanisms to a relatively large degree so that the insoluble particles in these compositions can migrate into the pore structure of substrates such as wood. Hybrid treatment compositions of the present invention do not have this limitation. With hybrid compositions, even coarse particles, i.e., particles that generally are too coarse too penetrate into the pore structure of wood substrates effectively by physical mechanisms alone, nonetheless are able to penetrate much more deeply into the substrate via other mechanisms that come into play. Again, and without wishing to be bound by theory, it is believed that chemical mechanisms attributable at least in part to equilibrium dynamics contribute to the ability of the initially coarse, insoluble material to be converted into a more mobile, more soluble complexed form that is able to penetrate better into the substrate.

Without wishing to be bound by theory, it is believed that an equilibrium occurring dynamically in the substrate among one or more insoluble and one or more soluble states is a key factor leading to this performance. At any one point in time, it might be true that only a portion of the metal biocide stoichiometrically corresponding to the amount of complexing agent is in soluble, complexed form(s), while the remainder tends to be in insoluble state(s) per the equilibrium. At such a point in time, the current dissolved portion is relatively mobile and, consequently, is more able to penetrate more thoroughly and uniformly into the substrate. For instance, dissolved metal biocide can penetrate into the cells of wood substrates quite effectively. The current insoluble metal biocide portion, in contrast, typically present in particulate form, is more fixed and less mobile. An insoluble form might tend to reside mainly in the pores of wood substrates, for example, with very little if any penetration into intact cells.

It is believed, however, that substantially all of the available metal biocide participates in equilibrium reactions such that differing portions of the metal biocide are continuously precipitating into one or more insoluble states and vice versa while other portions are being converted into one or more soluble, complexed states and vice versa. Over time, a much greater portion of the metal biocide than just that which can be bound by the complexing agent if not all of the metal biocide, is dissolved and mobile as a practical matter. In short, while only some of the metal biocide might be in the mobile, second complex state at any one point in time, dynamically at least substantially all of the metal biocide is mobile at some point in time. As successive portions are dissolved and mobilized, these portions are able to penetrate the substrate more uniformly and more thoroughly.

Examples of metals that can be used as metal biocide(s) in the hybrid preservative compositions of the present invention include one or more transition metal elements including the lanthanide and actinide series elements such as copper, strontium, barium, arsenic, antimony, bismuth, lead, gallium, indium, thallium, tin, zinc, chromium, cadmium, silver, gold, nickel, molybdenum, combinations of these, and the like. A preferred metal biocide is copper. Due to present regulatory concerns it is desirable to limit or avoid the use of Cr and/or As in residential applications. Accordingly, some embodiments of hybrid compositions of the invention are desirably at least substantially arsenic free, at least substantially chromium free, and/or at least substantially chromium and arsenic free. However, it is appreciated that the principles of the present invention still would be useful to help improve penetration of particulate forms and/or reduce the leaching of soluble forms of Cr and/or As from biodegradable substrates such as wood products, and therefore could greatly ease regulatory concerns associated with the use of wood preservatives incorporating one or both of these additives in some applications. For example, some amount of a homogeneous preservative composition including copper, chromium, and arsenic (known in the industry as CCA formulations), or ingredients corresponding to such compositions, could be incorporated into hybrid compositions to enhance efficacy in applications where permitted by regulation.

With respect to the relatively insoluble metal biocide portion of the hybrid preservative composition, one or more metal biocide(s) may be initially supplied as ingredient(s) to be incorporated into the composition, or a component of the composition, in a wide variety of solid forms. Alternatively, the relatively insoluble metal biocide material may be obtained from ingredients (s) that form insoluble material in situ. These in situ reactions may be the same or different than the equilibrium reactions between the relatively insoluble material and the soluble material. The solid material, and/or resultant solid material if formed in situ, may be in the form of precipitates, particles, pellets, granules, fibers, composites, combinations of these, and the like. Often, the solid material is supplied in the form of particles as these are economical to obtain or make, easy to handle in formulating and applying compositions, and/or readily form in situ.

With respect to selecting particles for initially formulating hybrid compositions of the present invention, a very wide range of particle sizes would be suitable in the practice of the present invention. Generally, any particle sizes that are reasonably compatible with desired manufacturing, packaging, and/or use techniques are suitable. More desirably, particles are small enough to penetrate at least into the largest pores of the substrate initially, after which equilibrium effects as discussed above can help the material achieve a more thorough and uniform substrate penetration. As general guidelines, particle size can be about 2 mm or less, desirably in a range from about $10^{-6}$ mm to 2 mm, more desirably from about $10^{-5}$ mm to about 0.1 mm, even more desirably from about $10^{-4}$ mm to about 0.05 mm.

The term particle size refers to the volume based particle size. For a specific particle, the volume based particle size is the diameter of a sphere having the same volume as such particle. For a particle sample comprising a population of particles, the volume based particle size is the mean volume based particle size of the volume distribution of the sample as determined using laser diffraction techniques, such as by using any of the laser diffraction particle size analyzers commercially available from Beckman Coulter (these include the LS™ 13 320 Series laser diffraction particle size analyzers, the LS™ 2 Series laser diffraction particle size analyzers which are preferred, and the LS™ 100Q laser diffraction particle size analyzer) for particle samples in which at least 90 weight percent of the particles have an average volume based particle size in the range from 0.4 micrometers to 2 mm. For smaller particle sizes, x-ray diffraction techniques may be used, optionally equipped with a synchrotron source for particle sizes in the range from 0.1 micrometers to about 4 micrometers.

The particles can have any kind of particle size distribution(s). For instance, in addition to some particle ingredients of the invention having normal distributions, other particulate ingredients used to formulate hybrid compositions may include particle size characteristics with two or more size distribution peaks. Combinations of particle ingredients with different or similar distribution profiles may also be used. For instance, the particulate ingredients may be a blend derived from relatively coarse grains and relatively fine grains. This might be desirable in embodiments where two different metal biocides are being used. Although supplying the particles in an extremely finely divided form to facilitate substrate penetration is not required, the particles optionally may be mechanically, physically, chemically, or otherwise sized to provide them in an alternatively desired particle size configuration.

The relatively insoluble material containing one or more metal biocides initially may be in a wide variety of chemical forms that are reactive with the relatively soluble material via equilibrium reaction(s). In some embodiments, the relatively insoluble material may be ionic or nonionic. In some embodiments, the relatively insoluble material may be crystalline, partially crystalline, or amorphous. When the relatively soluble material includes one or more complexes of one or more metal biocides, illustrative insoluble forms include pure metals, metal alloys, intermetallic compositions, composites, oxides, oxyhalides, oxyhydroxides, hydroxides, carbonates, formates, basic carbonates, quinolates, carbamates, omadines, borates, other salts, combinations of these, and the like.

For example, in the case of copper, suitable relatively insoluble material reactive with complexing agents include cuprous oxide, cupric oxide, copper hydroxide, copper carbonate, copper basic carbonate, copper oxychloride, copper-8-hydroxyquinolate, copper dimethyldithiocarbamate, copper omadine, copper borate, copper metal byproducts, copper sulfate, copper fluoroborate, copper fluoride, copper formate, copper acetate, copper bromide, copper iodide, copper basic phosphate, copper basic phosphor-sulfate, copper basic nitrate, combinations of these, and the like. Copper basic carbonate, which may be represented by the simplified formula $Cu(OH)_2$—$CuCO_3$, is an example of one preferred source of relatively insoluble copper.

In preferred embodiments, the relatively soluble state of the metal biocide is in the form of a metal complex. The complex is easily obtained by reacting a suitable source of the metal biocide with one or more complexing agents in an aqueous reagent. Suitable metal biocide sources include the sources identified above for insoluble forms of the metal biocide. The complexing agent helps dissolve and/or distribute the complexed metal biocide or metal biocide-containing species. The use of the complexing agent may be desirable even when the Cu is supplied from a highly water-soluble source inasmuch as the resultant complexes are more resistant to precipitation and/or settling during manufacture, packaging, storage, dilution with various water supplies, preserving treatments, and/or other handling. The use of complexing agents is a straightforward, economic way to dissolve the metal biocides in aqueous media and to facilitate a more uniform distribution of the metal biocide in the substrate.

The complexing agent is also referred to as a ligand, chelant, chelating agent, or sequestering agent in the field of coordination chemistry. The complexing agent is desirably one that bonds to the central metal-containing species, often an ion, through one or more atoms of the complexing agent. These bonds may be a combination of one or more different kinds of bonds such as coordination and/or ionic bonds. A wide variety of complexing agents may be used in the practice of the present invention. These include organic acids such as aspartic acid, citric acid, and oxalic acid; ammonia; polyamine functional compounds such as ethylenediamine; nitrogen-containing alcohols such as alkanolamines; combinations of these and the like. Examples of alkanolamines include monoethanolamine (MEA); isopropanolamine; 1-1- or 1,2-diaminoethanol; diethanolamine; dimethylethanolamine; triethanolamine (TEA); aminoethylethanolamine; combinations of these; and the like. The alkanolamines are presently preferred in complexes with copper. MEA, TEA, and mixtures of these are particularly preferred in which the molar ratio of MEA to TEA is in the range from 1:100 to 100:1, preferably 1:10 to 50:1 more preferably 1:2 to 25:1. In an illustrative embodiment, a molar ratio of 10:1 would be suitable.

The complex stability constant, $K_1$, is useful for evaluating the degree to which a metal or metal containing species can participate in equilibrium with a complexed counterpart of the metal or metal containing species. Generally, the complex stability constant K is given by the expression $K_1 = \log([LM]/[L][M])$, where L is the ligand, M is the metal or metal containing species in equilibrium with the complexed metal, and LM is the complexed metal. Generally, a ligand binds more strongly to the metal as $K_1$ increases. If $K_1$ is too high, the ligand may bind to the metal too strongly and may not participate in either the desired equilibrium reaction(s) to the degree that might be desired or in interactions with the substrate. When the $K_1$ is too high, the tendency of the complex to leach also tends to increase. On the other hand, if the $K_1$ is too low, then solubility of the complex and/or transport into the substrate might be inhibited to a larger degree than might be desired. Balancing these concerns, in more preferred embodiments, metal and corresponding ligand(s) are included for which $K_1$ at 25° C. is at least about 2.5, preferably at least about 3 at the low end and is less than about 6.5, preferably less than about 6, more preferably less than about 5.5 at the high end.

For example, the constant $K_1$ associated with MEA and $Cu^{+2}$ is about 4.5. MEA works very well in wood preservatives with copper because the $K_1$ value is quite suitable. Similarly, the combination of TEA and copper have a suitable $K_1$ of about 4.0. In contrast, the combination of EDA and copper has a $K_1=10$ and is much less desirable in this application, particularly if EDA is used alone as the only complexing agent, as EDA binds to copper very strongly, i.e., more than 100,000 times as strongly as MEA.

The complexing agent is used in an amount effective to form a complex only with a portion of the total metal biocide that will be present in the resultant hybrid composition. When the hybrid composition is obtained by blending homogeneous and heterogeneous constituents, or is otherwise obtained from multiple components, one or more of these components cumulatively may include a stoichiometric amount or stoichiometric excess of the complexing agent so long as the combination of all the components results in a stoichiometric deficiency overall. It is important to emphasize that many of the benefits of the hybrid approach, believed to be attributable to equilibrium effects between insoluble and soluble material, desirably involve a sufficient stoichiometric deficiency of the complexing agent relative to the metal biocide. If there is a stoichiometric excess of the complexing agent, substantially all of the metal biocide will be dissolved and will tend to stay that way. Even if there is a stoichiometric deficiency of complexing agent but the deficiency is too small, the resultant composition essentially behaves as a homogeneous solution as a practical matter without material realization of the significant hybrid benefits.

On the other hand, if the stoichiometric deficiency is too great, the resultant composition would include too much insoluble material relative to soluble material. The resultant composition would tend to behave too much like a heterogeneous composition without material realization of the penetration, size restrictions, or significant hybrid benefits.

Accordingly, it is desirable that preferred embodiments of hybrid formulations of the present invention include a sufficient amount of complexing agent such that at least about 20 weight percent but no more than about 95 weight percent, preferably at least about 30 weight percent but no more than about 90 weight percent, and more preferably at least about 50 weight percent to about 85 weight percent of the total amount of metal biocide is complexed. In one illustrative embodiment, using an amount of complexing agent such as MEA and/or TEA to complex about 60 weight percent of the metal biocide such as copper would be suitable. This embodiment would exhibit many hybrid benefits to a very high degree, including enhanced penetration relative to totally heterogeneous compositions and improved retention relative to totally homogeneous compositions.

The weight percent of metal biocide incorporated into the composition may vary over a wide range. If too little is used, then the biocidal activity of the composition may be less than might be desired. If too much metal biocide is used, then the excess metal biocide exceeding the saturation level of the substrate for retaining the biocide is wasteful and may tend to be more prone to leaching. Consequently, using greater amounts of the metal biocide in excess of the saturation level might offer little, if any, extra biocidal protection due to leaching of the excess. Stated differently, using lesser amounts of metal biocide within the capacity of the substrate to more strongly retain the biocide would provide just as much biocidal protection as using greater amounts but without being wasteful.

In some instances, it may be desirable to initially formulate the hybrid composition (or components thereof if formulated in two or more parts to be applied to substrates separately thus being combined in situ) in a more concentrated form to facilitate manufacturing, packaging, and shipping. The end user then would dilute the composition to the final desired concentration to treat wood products. Balancing such concerns, compositions of the present invention may include from about 0.02 to about 15 weight percent biocidal metal(s), more preferably 0.04 to about 11 weight percent metal(s) based on the total weight of the resultant composition. If the composition is to be formed upon combining two or more separate components, this weight percent is based upon the total weight of the components after being combined. Generally, weight percents higher than about 3 weight percent metal(s), more typically about 7 weight percent metal(s) represent more concentrated embodiments that might be diluted by the end user prior to a preservative treatment.

In calculating the weight percent metal(s) incorporated into a composition, only the weight of the metal(s) per se is/are used to make the calculation without inclusion of the weight of other species that might be included with the metal(s) in the metal source(s). For example, if 15 grams of copper basic carbonate deemed to have the simplified formula $Cu(OH)_2$—$CuCO_3$ is incorporated into a composition whose total weight is 100 g including the added copper basic carbonate, then the weight percent of copper in this composition is 8.6 weight percent.

The hybrid compositions, or components thereof, are formulated in a liquid carrier. Often, the compositions are aqueous or partially aqueous, and the liquid carrier for the treating solution is at least partially water. In many illustrative embodiments, the liquid carrier is at least 50 weight percent, preferably at least 75 weight percent, and more preferably at least 90 weight percent water. In addition to water, the liquid carrier of the preservative compositions may further include one or more optional solvents to help dissolve or disperse other composition ingredients. Such additional solvents are either fully miscible with water or are used in sparing amounts when it is desired to avoid phase separation among the components. Examples of such optional solvents include alcohols such as ethanol and isopropanol, tetrahydrofuran, acetonitrile, combinations of these, and the like.

The hybrid compositions may further include one or more other optional ingredients in order to enhance manufacture, use, performance, or the like. For example, metal biocides such as copper may not have as full a biocidal spectrum against microbes, fungi, pests, etc., as might be desired. Accordingly, one or more additional co-biocides may be incorporated into the preservative compositions in order to provide a fuller biocidal range. Additional co-biocides may include one or more of fungicidal, insecticidal, moldicidal, bactericidal, algaecidal biocides, and/or the like. These co-biocide(s) can be water soluble, partially water soluble, or water insoluble. If partially insoluble or insoluble, dispersants or chelating agents may be used to help disperse these in the preservative compositions.

Thus, a wide range of inorganic and/or organic biocides may be used in accordance with conventional practices. Extensive lists of suitable biocides are provided in the patent literature, including in U.S. Pat. No. 5,874,025; and U.S. Pat. Pub. Nos. 2006/0086284; 2006/0162611; 2005/0256026; and 2005/0249812. The respective entireties of these patent documents are incorporated herein by reference for all purposes. Particularly preferred co-biocides include quaternary ammonium salts and the azole materials, including triazoles and imidazoles. Benzalkonium chloride or carbonate is one preferred quaternary ammonium salt; didecyldimethylammonium chloride or carbonate is another commonly used quaternary ammonium salt. Exemplary azoles include tebuconazole and propiconazole.

As another performance concern, a problem with soluble or easily dispersed forms of metal biocides is that these may tend to more readily leach from treated, biodegradable substrates when exposed to rain or other sources of water. Advantageously incorporating a leaching-reducing agent into the impregnation composition dramatically reduces such leaching. Particularly preferred leaching-reducing agents are described in Assignee's copending U.S. Provisional Application having U.S. Ser. No. 61/007,614, filed Dec. 13, 2007 in the names of Kimberly S. Hayson, William C. Hoffman, Albert F. Joseph, Brian T. Keen for STRATEGIES FOR REDUCING LEACHING OF WATER-SOLUBLE METAL BIOCIDES FROM TREATED WOOD PRODUCTS, the entirety of which application is incorporated herein by reference for all purposes. According to this co-pending application and as used herein, preferred agents that reduce leaching of metal biocides are water soluble, are substantially nonionic in aqueous media, have a molecular weight (or a weight average molecular weight if the agent is present as a population distribution) greater than about 100, and have a vapor pressure less than that of water.

As used herein, water soluble with respect to the leaching-reducing agent means that a homogeneous solution may be prepared by dissolving 0.5 grams, 1.0 grams in some embodiments, and even 2.0 grams in some embodiments, of the agent(s) in 100 ml of distilled water, and then, when the resultant solution is stored at 25° C., at least 90% of the agent(s) remain in solution for at least two hours. When a single agent is to be used, the single agent to be used is dissolved in the water to assess water solubility. When a mixture of two or more agents are to be used in the treatment solution, an appropriate sample of the mixture in the intended proportions to be used is dissolved in the water to assess solubility.

Generally, molecular weight is one factor that impacts the ability of an agent to protect against leaching. If the molecular weight is too low, e.g., below about 100, or even below about 80, a material may not protect against leaching at all and may even increase leaching. On the other hand, agents of the invention having a molecular weight above about 100 tend to provide greater leaching protection. Indeed, leaching protection tends to increase as molecular weight, or weight average molecular weight as appropriate, increases. This means that agents with higher molecular weights generally can be used at lower usage rates to provide comparable or better leaching protection than agents with lower molecular weight. Accordingly, a leaching reducing agent of the present invention desirably has a molecular weight (or weight average molecular weight, as appropriate) of at least 100, more desirably at least about 150, even more desirably at least about 200, and even more desirably at least about 500.

However, there tends to be a maximum molecular weight beyond which use of an agent may become impractical. For instance, if the agent is too large, the impregnation solution may gel or otherwise be too viscous and/or impregnation may become unduly difficult. Accordingly, it is preferred that an agent of the present invention has a molecular weight (or weight average molecular weight, if appropriate) of no more than about 100,000, desirably no more than about 50,000, more desirably no more than about 30,000.

The leaching-reducing agent of the present invention also has a vapor pressure less than that of water at standard temperature. This helps ensure that the agent evaporates more slowly than water during a drying phase after impregnation, during the course of manufacture, and/or after an impregnated wood product is exposed to water (e.g., rain or the like) during its service life. In other words, the agent, as an organic phase, tends to concentrate relative to water as the relatively more volatile water evaporates faster. Without wishing to be bound, it is believed that the relatively concentrated organic phase, due to partition coefficient effects, helps to reduce the propensity for complexed metal biocide to be dissolved in the water that may be present. This enhances the ability of the wood to retain the metal biocide relative to the water, reducing leaching that might otherwise occur. Stated schematically, both the wood and water compete for the metal biocide. Leaching may have a greater tendency to occur when water is a relatively stronger competitor. However, in the presence of the additives of the present invention, the biodegradable substrates are relatively stronger competitors than they would be in the absence of the additives, resulting in less leaching.

Desirably, preferred leaching-reducing agents of the present invention have a vapor pressure of less than 15 mmHg, preferably less than 10 mmHg, more preferably less than 1 mmHg, and even less than 0.1 mmHg at 25° C. By way of comparison, water has a vapor pressure of about 24 mmHg at 25° C. Some embodiments of the leaching-reducing agents of the present invention by themselves may be in the form of solids at room temperature. Such materials tend to sublime to some very minor degree, but may be viewed as having a negligible vapor pressure well below 0.1 mmHg at 25° C. for purposes of the present invention.

Substantially nonionic leaching-reducing agents of the present invention may tend to include some nonionic and/or ionic impurities as prepared or as obtained from commercial sources, as the case may be. Taking into account the potential presence of such impurities, preferred substantially nonionic leaching-reducing agents of the present invention are those containing less than 5 weight percent, preferably less than 2 weight percent, and more preferably less than 0.5 weight percent of nonionic and/or ionic impurities. However, so long as at least one such substantially nonionic substance is used to help protect against leaching, preservative compositions optionally may include one or more ionic species if desired for a variety of purposes. Examples of such ionic species include metal salts, quaternary ammonium salts, other inorganic and/or organic salts, combinations of these, and the like, such as the polymeric quaternary ammonium borates containing PEG blocks described in U.S. Pat. Nos. 5,304,237 and 5,874,025.

In addition to the combination of characteristics mentioned above, preferred leaching reducing agents may also have one or more additional characteristics, either singly or in combination, to further enhance leaching protection. For instance, in some embodiments, it is preferred that the leaching reducing agents are substantially neutral. As used herein, "substantially neutral" means that a solution of 0.5 grams, preferably 1.0 grams, or more preferably 2.0 grams, of the agent or agent(s) dissolved in 100 ml of distilled water has a pH in the range of from about 4 to about 10, preferably from about 5 to about 9, more preferably about 6 to about 8 at 25° C. When a single agent is to be used, the single agent to be used is dissolved in the water to assess pH characteristics. When a mixture of two or more agents are to be used, an appropriate sample of the mixture in the intended proportions to be used is dissolved in the water to assess pH characteristics.

As another optional, desirable characteristic, preferred leaching-reducing agents are those including at least about 4 weight percent, more preferably at least about 4 to about 55 weight percent, and even more preferably at least about 20 to about 45 weight percent oxygen. Examples of these preferred agents include (poly)ethers and/or nonionic surfactants including one or more oxyalkylene units in the backbone and/or as substituents of the molecule. As used herein, the term "(poly)" with respect to an ether indicates that the ether may have one or more oxyalkylene units. The term "poly" without parentheses indicates that the material includes two or more oxyalkylene repeating units, which may be the same or different. In some embodiments, the ingredients that help to improve leaching resistance comprise a combination of a (poly)ether and a nonionic surfactant incorporating one or more of such oxyalkylene groups, respectively. Representative embodiments of (poly)ethers of the present invention comprise one or more linear, branched, and/or cyclic, divalent oxyalkylene repeating units, or combinations of these. The (poly)ethers may be homopolymers or copolymers of two or more copolymerizable materials. If made from two or more copolymerizable materials, the different materials may be incorporated into the (poly)ether randomly or in blocks.

In the practice of the present invention, a divalent, oxyalkylene unit generally has the formula —RO—, wherein R is any straight, branched, or cyclic alkylene or aralkylene, divalent moiety often including from 1 to 10, desirably 1 to 5, more desirably 1 to 3 carbon atoms. Repeating units with larger numbers of carbon atoms may be incorporated into the (poly)ether if desired. However, if the units include too many carbon atoms, or if the (poly)ether includes too large a percentage of repeating units having a relatively large number of carbon atoms, or if the agent is too large, the water solubility of and/or leaching protection provided by the (poly)ether may suffer. Examples include —CH$_2$O—, —CH$_2$CH$_2$O—, —CH$_2$CH$_2$CH$_2$O—, —CH$_2$CH(CH$_3$)O—, —CH(CH$_3$)CH$_2$O—, —CH$_2$CH(CH$_2$CH$_3$)O—, —CH(CH$_2$CH$_3$)CH$_2$O—, —CH$_2$CH(CH$_3$)CH$_2$O—, —CH(CH$_3$)CH$_2$CH$_2$O—, —CH$_2$CH$_2$CH(CH$_3$)O—, —CH$_2$CH(CH$_2$CH$_3$)CH$_2$O—, —CH(CH$_2$CH$_3$)CH$_2$CH$_2$O—, —CH$_2$CH$_2$CH(CH$_2$CH$_3$)O—, additional variations in which more than one substituent of the oxyalkylene backbone is an alkyl moiety, combinations of these, and the like. The (poly)ethers desirably have terminal groups selected from H; linear, branched or cyclic alkyl of 1 to 12 carbon atoms; alkoxy of 1 to 12 carbon atoms; and combinations of these. Often, a commercially available product will include more than one kind of —RO— moiety within individual molecules in those embodiments when the number of —RO— repeating units is greater than one on average. Additionally, commercially available products may include a population distribution of different (poly)ether molecules.

Suitable (poly)ethers are often commercially available as a mixture containing a distribution of (poly)ether polymers with varying number of repeating units and a corresponding variation in molecular weight. Preferred (poly)ether populations of this sort generally may have an average of at least two and preferably from about 1 to about 3000 of these divalent, oxyalkylene repeating units. In more preferred embodiments, the (poly)ethers have a sufficient number of these repeating units such that the (poly)ether material has a weight average molecular weight in the range from at least about 100 to about 50,000, preferably from about 300 to about 30,000, more preferably from about 500 to about 20,000.

The (poly)ether preferably includes at least one (poly)ethylene glycol (PEG). A PEG is a linear (poly)ether polymer incorporating two or more oxyethylene (EO) repeating units and may be represented by the formula $$R^1O\text{---}(CH_2CH_2O)_n\text{---}R^2$$

wherein each of $R^1$ and $R^2$ independently is H or straight, branched, or cyclic alkyl, preferably H or alkyl of 1 to 12 carbon atoms, often 1 to 3 carbon atoms; and n is 1 to 3000 and preferably is a number such that the PEG has a weight average molecular weight in the range of from at least about 100 to about 50,000, preferably from about 300 to about 30,000, more preferably from about 500 to about 20,000.

Another class of (poly)ether materials that would be useful in the practice of the present invention are copolymers at least incorporating one or more oxyethylene and one or more oxypropylene (PO) repeating units according to the formula $$R^3O\text{---}(CH(CH_3)CH_2O)_m\text{---}(CH_2CH_2O)_n\text{---}R^4$$

wherein each of $R^3$ and $R^4$ independently is H or straight, branched, or cyclic alkyl, preferably H or alkyl of 1 to 12 carbon atoms, often 1 to 3 carbon atoms; m is 1 to 3000; n is 1 to 3000; and m+n preferably is a number such that the PEG has a weight average molecular weight in the range of from at least about 100 to about 50,000, preferably from about 300 to about 30,000, more preferably from about 500 to about 20,000. Desirably, the ratio of m to n may be in the range from about 1:4 to about 4:1, preferably about 1:1.5 to 1.5:1. In this formula, any other isomer(s) of oxypropylene may be present.

Optionally, in addition to the oxyalkylene units, any (poly)ethers used in the practice of the present invention may further incorporate up to 70 weight percent, desirably up to 25 weight percent, more desirably up to 10 weight percent, and even more desirably up to 2 weight percent of other copolymerizable materials. Examples of such other materials are monomers that include free radically polymerizable functionality such as carbon-carbon double bonds. These materials include monomers such as olefins (ethylene, propylene, butadiene, etc.), (meth)acrylates, styrene-type materials, combinations of these, and the like.

Methods for preparing (poly)ether polymers, including PEG polymers and copolymers of EO and PO are known to those skilled in the art. In addition, the starting materials, often including EO, PO, butanol, glycerol, and hydrogen, are commercially available.

Specific examples of commercially available (poly)ether materials are the CARBOWAX PEG 8000 (weight average molecular weight of about 8000) and the CARBOWAX PEG 1000 (weight average molecular weight of about 1000) polyethylene glycol products commercially available from The Dow Chemical Co. Other examples include glycol ethers such as butoxy triglycol, tripropylene glycol butyl ether, tetraethylene glycol, as well as the glycol ethers available under the trade designation CELLOSOLVE (e.g., Butyl CELLOSOLVE Solvent and Hexyl CELLOSOLVE Solvent) from The Dow Chemical Co.

The amount of the leaching reducing agent incorporated into the preservative composition may vary over a wide range. Representative embodiments may include from about 0.01 to about 200, desirably 0.5 to about 50 parts by weight of the leaching reducing agent per one part by weight of the metal biocide. As is the case above in calculating the weight percent of metal biocide in the composition, the relative parts by weight of the leaching reducing agent relative to the metal(s) is based upon the weight(s) of the metal(s) themselves without inclusion of the weight of other species that might be included with the metal(s) in the metal source(s).

The leaching-reducing agent may also be in the form of, or further include in combination with another agent, one or more nonionic surfactants to help promote leaching resistance. In particular, embodiments of preservative compositions including both (poly)ether and a nonionic surfactant demonstrate excellent leaching resistance, even when only a relative minor proportion of the nonionic surfactant is used relative to the (poly)ether. Nonionic surfactants refer to compounds having at least one hydrophilic moiety coupled to at least one hydrophobic moiety wherein the surfactant carries no discrete cationic or anionic charge when dissolved or dispersed in the preservative composition.

A wide range of nonionic surfactants may be used. In preferred embodiments, the hydrophilicity of the nonionic surfactant is provided by a polyoxyalkylene moiety of the formula —$(R^5O)_w$— wherein $R^5$ is alkylene of 1 to 5 carbon atoms, particularly —$CH_2$— (methylene), —$CH_2CH_2$— (ethylene), propylene, isopropylene, butylene, or isobutylene; and w is often 1 to about 100. $R^5$ preferably is ethylene, propylene, or isopropylene. This polyoxyalkylene moiety is capable of strong hydrogen bonding with water, providing the desired hydrophilic characteristics.

The hydrophobicity of the nonionic surfactant is generally provided via a nonpolar moiety coupled to the hydrophilic moiety. Nonpolar desirably means that the moiety includes at least 6 carbon atoms to 100 carbon atoms, preferably at least 10 carbon atoms to 100 carbon atoms; and that there are no more than 2 hetero atoms such as O, S, N, P or the like per 6 carbon atoms, preferably per 10 carbon atoms, more preferably per 15 carbon atoms. In representative embodiments, the hydrophobic moiety is linear, straight, or cyclic alkyl, aryl, aralkyl; or alcohol. Preferred hydroxyl moieties are secondary.

A representative embodiment of a nonionic surfactant is an adduct of an EO or an EO/PO (poly)ether and an alcohol, desirably a secondary alcohol. Such an adduct may have the following formula:

$$R^6O\text{---}(R^7O)_p\text{---}R^9$$

wherein $R^6$ is a straight, branched, or linear nonpolar group, cyclic or aryl of 10 to 100, preferably 10 to 50 carbon atoms; each $R^7$ is independently an alkylene moiety of 1 to 4 carbon atoms, preferably 2 to 3 carbon atoms, and $R^9$ is H or a monovalent moiety comprising 1 to 20 carbon atoms, preferably 1 to 10 carbon atoms and may be non-aryl or aryl; and p is 1 to 200. Particularly preferred embodiments of such an adduct independently have the formulae $$R^{10}O\text{---}(CH_2CH_2O)_k\text{---}(CH(CH_3)CH_2O)_q\text{---}H$$

$$R^{10}O\text{---}(CH_2CH_2O)_k\text{---}(CH_2CH(CH_3)O)_q\text{---}H$$

$$R^{10}O\text{---}(CH_2CH_2O)_k\text{---}(CH(CH_2CH_3)CH_2O)_q\text{---}H$$

$$R^{10}O\text{---}(CH_2CH_2O)_k\text{---}(CH_2CH(CH_2CH_3)O)_q\text{---}H$$

wherein each $R^{10}$ independently is a hydrocarbon group of 10 to 50 carbon atoms; each k independently is 0 to 80; each q independently is 0 to 40 with the proviso that k+q is greater than or equal to 1. Also included are variants in which an adduct includes a mixture if branched oxyalkylene units contributing towards the total number of q repeating units or variants of these branched oxyalkylene units including two or more pendant alkyl substituents from one or more carbon atoms also contributing to the total number of q repeating units. Often, a commercially available product will include a population distribution of such adducts such that the values for molecular weight, k and q may be expressed as an average. In such mixtures, molecular weight refers to weight average molecular weight throughout this specification unless otherwise expressly noted.

Any amount of nonionic surfactant that is effective to help reduce leaching may be used in the preservative composition. It has been found, however, that leaching resistance is enhanced if the weight ratio of the (poly)ether to the nonionic surfactant is greater than about 1. Accordingly, the weight ratio of the (poly)ether to the nonionic surfactant is greater than 1:1, preferably from about 2:1 to about 50:1, more preferably from about 3:1 to about 20:1.

Other optional ingredients may also be beneficially used in the preservative composition in accordance with conventional practices. For example, during the course of manufacture, if metal vessels may be used to prepare, transport, store, or otherwise contact the composition, the compositions may include a corrosion inhibitor. Boron containing inhibitors such as boric acid used in corrosion inhibiting amounts have been found to be suitable for this purpose. Other adjuvants include dispersants, emulsifiers, binders, fixatives, water repellants, coloring agents, antioxidants, ultraviolet stabilizers, emulsifiers, antistatic agents, dessicants; precipitation inhibitors; buffers; fire retardants; combinations of these, and the like used in accordance with conventional practices.

Hybrid compositions of the present invention may be prepared using a variety of strategies. Illustrative strategies include but are not limited to the following. A single, one component composition can be prepared from ingredients comprising one or more metal biocides, one or more complexing agents, a liquid carrier, and one or more optional ingredients, wherein there is a sufficient stoichiometric deficiency of the complexing agent relative to the metal biocide such that the both soluble and insoluble forms of the metal biocide are in equilibrium. As described above, the stoichiometric deficiency of the complexing agent(s) desirably is such that at least about 20 weight percent but no more than about 95 weight percent, preferably at least about 30 weight percent but no more than about 90 weight percent, and more preferably at least about 50 weight percent to about 85 weight percent of the total amount of metal biocide is complexed. A substantial portion of the remainder that is not complexed will tend to precipitate. It is believed that the precipitate may take one or more forms, which may be the same and/or different than the solid form(s) in which the metal biocide was initially supplied as an ingredient to prepare the composition in the first instance.

It is beneficial to first combine the metal source(s) and the complexing agent at generally the desired concentration in a liquid carrier such as water with mixing to form the metal complex. Then, additional ingredients may be added in one or more stages. According to one mode of practice, the reaction to form the metal complex may be carried out below, at, or above room temperature. It may be desirable to avoid heating the reaction mixture too much to avoid thermal degradation of the complexing agent.

The solubility of the hybrid metal biocide constituents may depend upon the pH of the composition. In the case of copper with no complexing agent present, for instance, the copper may be too soluble in the liquid carrier at acidic pH values. Accordingly, in the case of copper, it is desirable that the composition have an alkaline pH to help ensure that at least a portion of the metal biocide is present as a precipitate. Unlike homogenous compositions for which strongly alkaline solutions having pH values of greater than about 10 might be more desirable, the hybrid compositions may be formulated at these as well as more moderate alkalinity, e.g., from about 7 to about 11, preferably about 7 to about 9.5, more preferably about 7 to about 8.5.

As an alternative strategy for preparing a hybrid composition, a homogeneous preservative composition comprising complexed metal biocide in a liquid carrier can be provided in the first instance. Illustrative examples of such compositions include the ACQ preservative compositions. Assignee's co-pending application cited above describes many suitable embodiments. Others are described in U.S. Pat. No. 4,929,454, the entireties of which are incorporated herein by reference for all purposes. Additional, commercially available examples are available under the trade designations NATUREWOOD (Osmose, Inc.) and PRESERVE (Chemical Specialties Inc.). Then, a sufficient amount of insoluble material comprising metal biocide is added such that the complexing agent that is present is in a suitable stoichiometric deficiency after the addition. Additional optional ingredients may also be added, such as dispersants or even complexing agent(s), or the like, if not already present or not present in desired amounts.

According to another strategy for preparing a hybrid composition, a heterogeneous preservative composition can be provided in the first instance. These compositions typically include insoluble particles dispersed in a liquid carrier, wherein the particles comprise one or more metal biocides. One or more additional optional ingredients, such as the additional optional ingredients described herein, may also be included in these compositions. Illustrative examples of heterogeneous preservative compositions are described in U.S. Pat. Publication Nos. 2004/0258767; 2005/0118280; 2005/0249812; 2005/0265893; 2006/0086284; 2006/0112850; and 2006/0147632, the entireties of which are incorporated herein by reference for all purposes. Additional, commercially available examples of these heterogeneous compositions are available under the trade designation MICROPRO (Osmose, Inc.). Then, a stoichiometric deficiency of one or more complexing agents may be added to the heterogeneous composition in order to dissolve only a portion of the insoluble metal biocide particles. Additional optional ingredients may also be added, such as dispersants or even complexing agent(s), or the like, if not already present or not present in desired amounts.

As another strategy for preparing a hybrid composition, separate heterogeneous and homogeneous compositions can be prepared. These can be blended together to form a hybrid composition. The individual compositions are formulated so that the resultant blend has the desired stoichiometric deficiency of complexing agent(s) relative to metal biocide, for example. The compositions may be pre-blended prior to treatment and then applied in hybrid form. As another alternative, the components can be applied stepwise to the substrate so that the hybrid composition forms in situ.

The preservative compositions may be prepared, stored, and/or shipped initially as one or more concentrates (e.g., one part or two part concentrates) if desired. The concentrate(s) can then be combined if more than one is used and diluted for treatment of biodegradable products. A wide range of concentration/dilution schedules may be used. For example, the concentrate may be at least 5, desirably 5 to 500, more desirably 5 to 50, and most desirably 6 to 40 times more concentrated than the diluted form of the composition that will be used to actually treat biodegradable products. At the time of dilution, a wide range of liquids can be used for dilution. Preferred dilution liquids include water and/or water miscible liquids. Water immiscible materials should be used sparingly so as to avoid phase separation. For economical reasons, using water by itself would be suitable in most instances. If the dilution water includes species that might induce undue precipitation of the metal biocide(s) or other ingredient(s) of the compositions, it may be desirable to treat the water prior to dilution. Representative examples of treatments include one or more of physical or chemical filtering, extraction, distillation, reverse osmosis, softening, other mass transfer techniques for removing impurities, and the like. Precipitation inhibitors may also be included in the composition, if desired.

Concentrates may be prepared in accordance with conventional methodologies, such as according to the methodology of AWPA Standard P5-07 (most recent version (referring to standard P5 issued in 2007)). The optional anti-leaching agent(s) may then be added to the concentrate at any time prior to, during, and/or after dilution to the final concentration that will be used to carry out the impregnation treatment. The agent(s) can be directly added to the concentrate or pre-dissolved in a suitable liquid carrier (often water) and then added to the concentrate. The anti-leaching agent(s) may be added quickly or slowly over a time period extending from ten seconds to 8 hours. Whether added quickly or slowly, the ingredients desirably are added with thorough mixing. Moderate heating may be used to help obtain a homogeneous composition. Because concentrates generally have long shelf-life, the concentrates can be stored for considerable periods of time before addition of the anti-leaching agent(s).

The preservative compositions of the present invention of any embodiments can be used to treat a wide range of natural and synthetic biodegradable products in a wide range of applications. Examples of cellulosic embodiments of biodegradable products include but are not limited to paper, cardboard, rope, veneer, lumber, manufactured timbers, cellulosic composites, engineered lumber, and sheet goods such as plywood, hardboard, particleboard, chipboard, fiberboard, strandboard, paneling, and the like. Representative end uses include residential, commercial, industrial, and marine interior or exterior applications such as construction lumber, trim, siding, decking, beams, railway sleepers, railroad ties, bridge components, jetties, wooden vehicles, docks, claddings, boxes, pallets, telephone poles, windows, doors, boats and ships, sheathing, foundation piles, posts, fences, marina structures, and other structures vulnerable to decay due to one or more of insects, fungi, microbes, and/or weathering.

The preservative compositions can be used to treat biodegradable products using a variety of treatment methods. These include manual methods such as spraying, brushing, immersion, pouring processes such as curtain coating, and the like. These also include automated methods such as pressurized impregnation, alternating pressure impregnation, vacuum impregnation, double vacuum impregnation, and the like. For synthetic wood products, the preservative compositions can be intermixed with other components used to form the products and/or used to impregnate components of such products prior to assembly. According to one illustrative method, a biodegradable product may be treated in accordance with AWPA T1-02 (commercial treating standard from year 2002).

Optionally, recognizing that a significant portion of leaching occurs initially from wood products with respect to excess metal biocide present above the saturation level, a treated wood product can be pre-leached, such as by contact with water for a suitable period, if desired. Such pre-leaching can occur via spraying, immersion, or the like. Pre-leaching may occur under ambient conditions or may occur at elevated or reduced pressures and/or elevated or reduced temperatures. Agitation may be used to accelerate the pre-leaching effect. Illustrative pre-leaching time periods may range from 20 seconds to ten days.

The leaching performance of compositions of the present invention may be evaluated according to different test methodologies. One current, widely accepted test methodology is set forth in AWPA E11-97. However, this test methodology requires extensive time (over 300 hours) and expense to complete just one test. These extensive time and expense burdens practically limit the number and rate of testing that can be carried out in an economically rationale fashion. Consequently, these burdens have limited acquisition of knowledge and slowed development in the field of preservative compositions for wood products.

An alternative method (hereinafter referred to as the Accelerated Leaching Test) provides more rapid evaluation of leaching characteristics of these compositions from cellulosic substrates. The test is not only rapid but much more cost effective than using more rigorous methods that extend over lengthy testing periods. The Accelerated Leaching Test makes it economical to gather data for multitudes of samples in a short time at relatively minor expense. Leaching data obtained from the Accelerated Leaching Test has been correlated to the more burdensome industry standard test of AWPA E11-97 and a very high correlation has been found based on the same rankings of samples according to percent metal leached. The Accelerated Leaching Test has greatly expanded the opportunity to acquire leaching knowledge about preservative compositions at an increased rate. Use of the method to acquire leaching data is a significant advantage.

According to the method, a sample of the treating composition under investigation is used to impregnate a cellulosic substrate. The treating composition may incorporate a metal biocide such as copper, and this accelerated test may be used to evaluate how the copper leaches from an impregnated sample. Sample preparation and impregnation may occur according to AWPA standard E10-01. The impregnated sample blocks are then allowed to dry overnight at room temperature followed by placing in an oven at 35° C. for 5 days to help fix a portion of one or more components such as the metal biocide directly or indirectly to the substrate. The term "fix" means chemically and or physically bonding the component to the substrate. Fixation, for instance, will tend to occur naturally when a metal-containing biocide is in contact with a dry substrate over a period of time, but fixation is accelerated by a thermal treatment.

After fixation, six of the impregnated sample blocks are immersed in 0.30 liters of distilled water for a period of 30 minutes to 72 hours at 25° C. with agitation to assess leaching. Agitation is provided by Innova 4000 Incubator Shaker. The agitation is an important feature that helps to accelerate the testing progress. As a result of agitating the immersed sample during the leaching period, the leaching characteristics of the tested sample can be correlated with a high degree of confidence to the leaching characteristics of corresponding impregnated products in the field. At one or more times such as prior to the beginning of the test, one or more times during, and/or after the leaching period, the water may be tested for Cu concentration to assess the degree of leaching from the sample.

Using the Accelerated Leaching Test has led to significant gains of knowledge. In particular, the test has been used to show that wood products have a saturation point for impregnation with a metal biocide such as copper. In practical effect, the data indicates that wood products have a finite capacity to bind a Cu impregnant relatively strongly. Any excess Cu impregnant beyond the saturation level will be bound less strongly and will be much more prone to leach in the field. Saturation is shown by various data. One class of supporting data shows that most leaching occurs very quickly, within the first 22 hours in real time. Thereafter, the rate of leaching slows tremendously and the Cu content of the wood product is much more stable. This is consistent with the view that excess Cu beyond the saturation level is held loosely and will leach out of wood relatively quickly.

The various aspects of the present invention will now be described with respect to the following illustrative examples. In the following examples all percentages and parts are by weight unless otherwise expressly indicated. All examples were done at ambient temperature that typically ranged from 20° C. to 25° C. unless otherwise noted.

EXAMPLE 1

Preparation of Wood Treating Concentrate

ACQ-C Wood treating concentrate was produced by adding 765 grams of Monoethanolamine (MEA) to a one-gallon container. Glass or polyethylene containers are preferred. 1554 grams of water was added to the MEA and mixed. Then 384 grams of Copper basic Carbonate was added to the mixture and stirred well to make sure that the Copper basic Carbonate was completely dissolved before proceeding to the next step. 159 grams of boric acid was added and stirred as a corrosion inhibitor. 138 grams of benzalkonium Chloride (Fluka 12060, purum, available from Fluka Chemical Corp., Milwaukee, Wis.) was added and stirred.

EXAMPLE 2

Preparation of Treating Solutions

Wood treating concentrate of Example 1 was diluted to 6/1, 10/1, 17/1 and 28/1, respectively, by weight using distilled water. While maintaining stirring, $CO_2$ in the form of dry ice was added to each solution until a pH between 8.8 to 9.2 was achieved.

EXAMPLE 3

Preparation of Treating Solutions with Polyethylene Glycol as Additive to Provide Additional Protection Against Leaching A treating solution at a dilution of 28/1 by weight was prepared as described in Example 2, except that 3% by weight of polyethylene glycol having a weight average molecular weight of about 8000 (CARBOWAX PEG 8000 commercially available from The Dow Chemical Co.) was also dissolved in the diluted solution. The solution was diluted first, and then the PEG was added.

EXAMPLE 4

Wood Blocks

Two types of wood blocks were obtained and prepared for experimentation. Treated lumber available under the trade designation "PROWOOD MICRO" as manufactured by Universal Forest Products (Grand Rapids, Mich.) was used to prepare wood blocks used as Sample sets A, B1, B2, and C. This commercially available treated lumber includes copper and quaternary compounds as active biocides. The copper is micronized, being incorporated into the lumber as finely ground particles. Select untreated Southern Yellow Pine wood was purchased and used to prepare wood blocks used for Sample sets D through H and Comparative examples 1 through 4. Wood chosen for all examples was of consistent grain and texture. Approximately ¾ inch by ¾ inch by ¾ inch wood blocks, as the case may be, were obtained from treated or untreated lumber sources. Blocks were selected for testing and placed in a constant humidity chamber overnight. The humidity was maintained between 50 to 60%.

EXAMPLE 5

Treating Wood Blocks of Sample Sets A Through C and Comparative Samples 1-4

For each sample set, nine knot and defect free blocks of Example 4 were chosen for treatment. Blocks were weighed and staged for treatment. The block weights had a standard deviation of +/−0.2 grams. The starting copper content of the micronized copper treated blocks (Sample sets A through C) was approximately 0.26% (digestion and determined by Inductively Coupled Plasma (ICP)). Thus, the initial total CuO pcf (as used herein, the term "pcf" means pounds per cubic foot and in this context refers to the pounds of impregnated copper metal biocide per cubic foot of substrate expressed in terms of CuO as is common in the industry) was about 0.12 for these blocks. The blocks of Sample Set A were not further treated with treatment solution, and thus were heterogeneous samples only treated with the micronized copper and quaternary biocides. The wood blocks of Sample Sets B1 and C, however, were treated with 28/1 and 17/1 treatment solutions of Example 2 to prepare hybrid treated blocks of the present invention. The wood blocks of Sample Set B2 were treated with the 28/1 treatment solution including PEG according to Example 3.

To treat each set of blocks, the nine blocks were placed in the bottom a 500 ml Erlenmeyer flask with side arm. A perforated flexible plastic weighing dish was wedged on top the blocks to keep them submerged when the wood treating solution was later added. A 250 ml pressure-equalizing addition funnel containing 200 ml of wood treating solution was connected to the top of the Erlenmeyer flask. The flask side arm was connected to house vacuum that was set at 250 mmHg. The vacuum was applied for 20 minutes while being maintained at 250+/−5 mmHg. After 20 minutes the wood treating solution was added to the blocks. After all the solution was added, the vacuum was turned off. The blocks remained in the wood treating solution for 30 minutes. After 30 minutes the solution was removed from the blocks. Each side of each block was slightly dabbed on a paper towel to remove any excess liquid. Each hybrid block was then weighed and placed on a rack to dry. After each set of blocks sat overnight at room temperature they were place in a forced air convection oven for 5 days with the temperature maintained at 35° C.+/−1°. A container of distilled water was placed in the bottom of the oven to help control the rate of drying of the blocks.

The total active Copper applied in to the blocks of Sample Sets $B_1$, $B_2$ and C includes both the micronized copper originally present as commercially supplied as well the soluble copper applied in the respective solution treatment of this Example. Example $B_2$ was the same as $B_1$ except 3% PEG was dissolved in the treating solution per using the treating solution of Example 3.

In practical effect, the impregnation of Sample Sets B1, B2, and C illustrate an illustrative mode of practice in which a hybrid treatment is carried out sequentially, and the hybrid character of the treatment is realized in situ on the substrate. Firstly, the wood blocks used in these sample sets were initially impregnated with micronized copper. Then, the wood blocks were impregnated with a solution of complexed copper to yield the hybrid treatment in situ. Sequential treatments can be carried out in other ways. For instance, the solution can be used first, followed by micronized copper. An illustrative one-step treatment in which the hybrid formulation is pre-formed and then used for treatment is described further below.

EXAMPLE 6

Comparative Wood Blocks

For comparison purposes, the 6/1, 10/1, 17/1, and 28/1 diluted solutions prepared in Example 2 were used to impregnate respective Comparison Sample Sets 1 through 4 of the untreated wood blocks obtained from Example 4. The impregnation procedures of Example 5 were used. Thus, the resultant impregnated wood blocks of the sample sets included only copper and quaternary biocide from solution impregnation and did not involve co-impregnation with micronized copper. Consequently, these blocks were impregnated with homogeneous solutions. Sample Set A, described above is also a comparative, as it includes only impregnation with micronized copper and did not involve co-impregnation with complexed copper or other form of dissolved copper.

EXAMPLE 7

Copper Leaching Testing

After 5 days the blocks prepared in Examples 5 and 6 were removed from the oven. For each Sample Set, the 6 blocks with the closest absorbed weights were placed in a corresponding pint jar and 300 mls of distilled water were added to determine copper leaching. The jars were placed on an oscillating shaker and agitated at 120 rpm for 22 hours. After removing each jar from the shaker, a sample of the leaching solution was filtered and ppm (parts per million on a weight basis) copper determined by ICP analysis. The leaching results of Sample Sets A-C and Comparative Examples 1-4 are shown in Table 1.

TABLE 1

Two Step Hybrid Wood Treating Copper Leaching Study

| | Treating Solution used to impregnate the blocks | Average Treating Solution Absorbed Per Block (g) | Concentration of Cu in the treating solution used to treat blocks, expressed in terms of CuO (g/100 g soln) | Total Active Copper applied (CuO %), soluble plus insoluble (pcf) | Amount of soluble copper as percent of total Cu applied to blocks in a set | Total Cu Leaching from all tested blocks in a set, PPM, 22 hr | Comments |
|---|---|---|---|---|---|---|---|
| Comparative Example 1 | ACQ Concentrate 6:1 Dilution | 4.38 | 1.32 | 0.52 | 100 | 325 | |
| Comparative Example 2 | ACQ Concentrate 10:1 Dilution | 4.24 | 0.84 | 0.32 | 100 | 140 | |
| Comparative Example 3 | ACQ Concentrate 17:1 Dilution | 4.19 | 0.51 | 0.19 | 100 | 56 | Expected Cu leaching for 0.25 pcf (% CuO) interpolated from Comparative Examples 2 and 3 is 98 ppm Compare this expected leaching at 0.25 pcf to the leaching observed for B1 and B2. |
| Comparative Example 4 | ACQ Concentrate 28:1 Dilution | 3.91 | 0.34 | 0.12 | 100 | 20 | |
| Example A | None (micronized copper only) | 0 | 0 | 0.12 | <5% (estimated) | 5 | |
| Example B1 | ACQ Concentrate at 28:1 Dilution | 4.14 | 0.34 | 0.25 | 52 | 24 | Note that a 48% reduction in the soluble copper resulted in a 75% reduction in copper leaching |
| Example C | ACQ Concentrate at 17:1 Dilution | 4.22 | 0.51 | 0.32 | 63 | 49 | Note that a 37% reduction in the soluble copper resulted in 65% reduction in copper leaching |

TABLE 1-continued

Two Step Hybrid Wood Treating Copper Leaching Study

| | Treating Solution used to impregnate the blocks | Average Treating Solution Absorbed Per Block (g) | Concentration of Cu in the treating solution used to treat blocks, expressed in terms of CuO (g/100 g soln) | Total Active Copper applied (CuO %), soluble plus insoluble (pcf) | Amount of soluble copper as percent of total Cu applied to blocks in a set | Total Cu Leaching from all tested blocks in a set, PPM, 22 hr | Comments |
|---|---|---|---|---|---|---|---|
| Example B2 | ACQ Concentrate at 28:1 Dilution + 3% PEG 8000 | 3.91 | 0.34 | 0.24 | 50 | 13 | Note that a 48% reduction in the soluble copper with addition of 3% PEG resulted in a 86% reduction in copper leaching |

Note:
As used in Table 1 pcf = 62.4 GC/100 V, where pcf is pounds per square foot of the copper incorporated into the substrate per cubic foot of substrate expressed in terms of CuO, G is the weight of solution absorbed in grams, C is wt % CuO in solution, and V is volume in mL.

Hybrid Sample Sets $B_1$, $B_2$ and C, where the copper has been applied in a two-step process within the spirit of the invention, show significantly less copper leaching than Comparative Sample Sets 1 through 4, in which all the copper was applied in a fully soluble state. In fact, the reduction in copper leaching shown by Sample Sets $B_1$, $B_2$ and C is proportionately more than would have been predicted relative to the reduction in soluble copper applied. In addition, when split open, the blocks of Sample Sets $B_1$, $B_2$ and C show a uniform green color (indicative of dispersed copper) and the absence of large particles of un-dissolved copper basic carbonate as are observed in the un-homogenously treated blank, example A. This increased copper dispersion was verified by microscopic examination. The wood blocks of Comparative Sample A had low leaching as is characteristic of micronized copper, but the micronized copper was poorly distributed. Those blocks did not show a uniform green color when split open. Green streaks and large particles of un-dissolved copper could be seen via optical examination. The poor penetration of the micronized copper into the wood blocks of Comparative Sample Set A indicates that the micronized copper in those blocks would have less bioefficacy than the more thoroughly dispersed, micronized copper in the hybrid blocks of the invention.

EXAMPLE 8

Preparation of Hybrid Treating Composition D

Wood treating concentrate of Example 1 was diluted to 28/1 on a weight basis using distilled water. Copper Basic Carbonate was added to the 28/1 solution to increase only the copper basic carbonate to be equivalent to the copper basic carbonate present in a wood treating concentrate diluted to 17:1. This procedure resulted in a suspension with both soluble and insoluble copper basic carbonate. ICP analysis determined that the soluble copper was 69% of the total copper added.

EXAMPLE 9

Preparation of Hybrid Treating Composition E

Hybrid Treating Composition E was prepared using the procedure of Example 8 except that 3% by weight Polyethylene Glycol (CARBOWAX PEG 8000) was dissolved in the resulting suspension based upon the total weight of the solution. Soluble copper was 67% by weight of the total copper added via ICP analysis.

EXAMPLE 10

Preparation of Hybrid Treating Composition F

ACQ wood treating solution was produced by adding 9.6 grams of Monoethanolamine and 2.41 grams of Triethanolamine to a gallon container. About 34.4 grams of water was added to the amines and mixed. Then 7.7 grams of copper basic carbonate was added to the mixture and stirred well. About 3.2 grams of boric acid was added and stirred as well as 2.8 grams of FLUKA 12060 quaternary biocide. This mixture was diluted by adding 1680 grams of water to give a 28/1 solution (by weight). While maintaining stirring, $CO_2$ in the form of dry ice was added to the admixture until a pH between 9.2-8.8 was achieved. This admixture is comparable to 28/1 ACQ diluted solution (on a weight basis) in terms of total copper applied to the substrate. The soluble copper was 61% of the total copper added via ICP analysis.

EXAMPLE 11

Preparation of Hybrid Treating Composition G

ACQ wood treating solution was produced by adding 19.2 grams of Monoethanolamine and 4.8 grams of Triethanolamine to a gallon container. About 68.8 grams of water was added to the amines and mixed. Then 15.4 grams of copper basic carbonate was added to the mixture and stirred well. About 6.4 grams of boric acid was added and stirred until completely dissolved. Then 5.5 grams of FLUKA 12060 quaternary biocide was added. This mixture was diluted to a 17/1 dilution by adding 2040 grams of water. The soluble copper was 76% of the total copper added via ICP analysis.

EXAMPLE 12

Preparation of Hybrid Treating Composition H

Suspension D was used for Composition H except the admixture was diluted 1 to 1 on a weight basis with water. This resulted in a total copper basic carbonate level equivalent to that found in a 35:1 dilution on a weight basis. The soluble copper was 68% of the total copper applied via ICP analysis.

EXAMPLE 13

General One Step Hybrid Treating of the Wood Blocks

Nine knot and defect free untreated wood blocks were chosen to prepare Sample Sets using each of Hybrid Treating Compositions D through H. For each Sample Set, the block weights had a standard deviation of +/−0.2 grams. Blocks were weighed and placed in the bottom a 500 ml Erlenmeyer flask with side arm. A perforated flexible plastic weighing dish was wedged on top the blocks to keep them submerged when the wood treating solution was later added. A 250 ml round bottom flask containing 200 ml of wood treating solution was connected to the top of the Erlenmeyer flask by flexible tubing. Continuous stirring was maintained. The flask side arm was connected to house vacuum that was set at 250 mmHg. The vacuum was applied for 20 minutes while being maintained at 250+/−5 mmHg. After 20 minutes the wood treating solution was added to the corresponding Sample Set of blocks. After all the solution was added, the vacuum was turned off. The blocks remained in the wood treating solution for 30 minutes. After 30 minutes the solution was removed from the blocks. Each side of each block was slightly dabbed on a paper towel to remove any excess liquid. Each block was then weighed and placed on a rack to dry. After each set of blocks sat overnight at room temperature, they were place in a forced air convection oven for 5 days with the temperature maintained at 35° C.+/−1°. A container of distilled water was placed in the bottom of the oven to help control the rate of drying of the blocks.

This treatment regime illustrates one mode of practice of the invention involving a one-step process for impregnation. Leaching for each Sample Set prepared from Hybrid Treating Compositions D through H, respectively, were tested for leaching using the procedures of Example 7. The total applied copper (pcf as CuO), % soluble copper, and copper leaching are shown in Table 2 for each Sample Set. The copper leaching in examples D through H are all substantially less than the appropriate Comparative Sample Sets 3 and 4, Table 1. More over surprisingly, the reduction in copper leaching exceeds that expected by the reduction in soluble copper. Good penetration and dispersion of copper was observed in all examples, indicating good bio-efficacy potential. The penetration and dispersion was verified by microscopic examination. Example E is the same as example D, except 3% PEG 8000 was added to the formulation. A further reduction in copper leaching was observed using PEG.

TABLE 2

One Step Hybrid Wood Treating: Copper Leaching [Select Knot Free Pine]

| | Additive | | Average Treating Solution Absorbed Per Block (g) | Concentration of Cu in the treating solution used to impregnate blocks expressed in terms of CuO (g/100 g soln) | Total Active Copper Oxide applied to blocks in a set, soluble plus insoluble (pcf) | Amount of Soluble Copper as percent of total copper applied to blocks in a set | Total Cu Leaching from all blocks in a set, PPM, after 22 hr | Comments |
|---|---|---|---|---|---|---|---|---|
| Example D | ACQ Concentrate 28:1 Dilution with added Copper basic carbonate to equivalent 17:1 | | 4.47 | 0.51 | 0.21 | 69 | 23 | A 31% reduction in soluble copper resulted in at least a 59% reduction in leached copper relative to Comparative example 3, table 1, which included 0.19 pcf of soluble Cu. |
| Example E | ACQ Concentrate 28:1 Dilution with added Copper basic carbonate to equivalent 17:1 | 3% PEG 8000 | 4.00 | 0.51 | 0.18 | 67 | 15 | A 33% reduction in soluble copper with additive resulted in a 73% reduction in leached copper. |
| Example F | MEA/TEA Hybrid Copper Basic Carbonate Diluted 28:1 | | 3.90 | 0.34 | 0.12 | 61 | 9 | A 39% reduction in soluble copper resulted in a 55% reduction in leached copper. |
| Example G | MEA/TEA Hybrid Copper Basic Carbonate Diluted 17:1 | | 3.92 | 0.51 | 0.18 | 76 | 22 | A 24% reduction in soluble copper resulted in a 60% reduction in leached copper. |
| Example H | ACQ Concentrate 28:1 Dilution with added Copper basic carbonate to equivalent 17:1 diluted 1:1 with water [Total Copper Basic Carbonate equivalent to 35:1 dilution] | | 4.16 | 0.26 | 0.10 | 68 | 7.5 | A 16% reduction in total copper and a 32% reduction in soluble copper resulted in a 62% reduction in leached copper. |

*Actual soluble copper determined by ICP.
Note:
pcf = 62.4 GC/100 V, where G is wt. of soln absorbed in g, C is wt % CuO in soln, V is volume in mL.

What is claimed is:

1. A preservative composition for treating biodegradable substrates, comprising a first phase, a second phase, a metal biocide, at least one complexing agent, and at least one water soluble, substantially nonionic leaching-reducing agent, wherein:
   (a) the first phase comprises at least a first portion of the metal biocide,
   (b) the second phase comprises at least a second portion of the metal biocide,
   (c) the complexing agent is present in sufficient stoichiometric deficiency to complex only a portion of the metal biocide, and wherein the complexing agent and the metal biocide have a complex stability constant $K_1$ in the range from 2.5 to 6.5,
   (d) at least a portion of the metal biocide in the first phase is in equilibrium with at least a portion of the metal biocide in the second phase; and
   (e) the at least one water soluble, substantially nonionic leaching-reducing agent having a molecular weight at least 100 and having a vapor pressure less than that of water at 25° C., said composition including an amount of the substantially nonionic leaching-reducing agent effective to reduce leaching of the complexed metal biocide from a biodegradable substrate impregnated with the composition relative to an otherwise identical composition lacking the substantially nonionic leaching-reducing agent.

2. The composition of claim 1, wherein the first phase comprises a liquid phase and a portion of the metal biocide in the first phase comprises a soluble metal complex.

3. The composition of claim 2, wherein the second phase comprises particles and an additional portion of the metal biocide is included in the particles.

4. The composition of claim 3, wherein the particles are solid.

5. The composition of claim 2, wherein the soluble metal complex is derived from ingredients comprising a source of the metal biocide and a complexing agent comprising triethanolamine.

6. The composition of claim 2, wherein the soluble metal complex is derived from ingredients comprising a source of the metal biocide and a complexing agent comprising triethanolamine and monoethanolamine.

7. The composition of claim 6, wherein the weight ratio of the monoethanolamine to the triethanolamine is in the range from about 1:2 to about 25:1.

8. The composition of claim 2, wherein the at least one complexing agent is present in a stoichiometric deficiency such that from about 20 weight percent to about 95 weight percent of the metal biocide is soluble in the liquid phase.

9. The composition of claim 1, wherein the metal biocide comprises copper.

10. The composition of claim 1, wherein the composition has a pH in the range from about 7 to about 8.5.

11. The composition of claim 2, wherein the soluble metal complex is derived from ingredients comprising a source of the metal biocide and a stoichiometric deficiency of the at least one complexing agent, wherein the complex stability constant for the metal biocide and the at least one complexing agent is in the range from 3 to 6.

12. The composition of claim 1, wherein the substantially nonionic leaching-reducing agent includes at least 10 weight percent oxygen.

13. The composition of claim 1, wherein the substantially nonionic leaching-reducing agent comprises one or more oxyalkylene units.

14. The composition of claim 1, wherein the composition includes from about 0.01 to about 200 parts by weight of the substantially nonionic leaching-reducing agent per one part by weight of the metal biocide.

15. The composition of claim 1, wherein the substantially nonionic leaching-reducing agent comprises a (poly)ether.

16. The composition of claim 1, wherein the substantially nonionic leaching-reducing agent comprises a (poly)ether and a nonionic surfactant.

17. The composition of claim 15, wherein the (poly)ether comprises a (poly)ethylene glycol having at least one oxyethylene group and including terminal groups selected from H; linear, branched or cyclic alkyl; and combinations of these.

18. The composition of claim 17, wherein the (poly)ether has the formula:

$$R^1O-(CH_2CH_2O)_n-R^2$$

wherein each of $R^1$ and $R^2$ independently is H or straight, branched, or cyclic alkyl, and n has an average value such that the (poly)ether has a weight average molecular weight in the range of 100 to 50,000.

19. The composition of claim 15, wherein the (poly)ether has a weight average molecular weight in the range from about 300 to about 30,000.

20. The composition of claim 15, wherein the (poly)ether has a weight average molecular weight in the range from about 500 to about 20,000.

21. The composition of claim 16, wherein the nonionic surfactant is an adduct of a reactant comprising at least one oxyalkylene unit and an alcohol.

22. The composition of claim 21, wherein the alcohol is a secondary alcohol.

23. An aqueous preservative composition for treating biodegradable substrates, said composition being derived from ingredients comprising an aqueous liquid carrier, at least one metal biocide, at least one water soluble, substantially nonionic leaching-reducing agent, and at least one complexing agent, wherein:
   said at least one complexing agent being present in a stoichiometric deficiency relative to the at least one metal biocide under conditions such that a portion of the metal biocide is incorporated into a soluble metal complex contained in the liquid carrier and at least a portion of the metal biocide is incorporated into a separate phase from the liquid carrier, and wherein the complexing agent and the metal biocide have a complex stability constant $K_1$ in the range from 2.5 to 6.5; and
   the at least one water soluble, substantially nonionic leaching-reducing agent having a molecular weight of at least 100 and having a vapor pressure less than that of water at 25° C., said composition including an amount of the substantially nonionic leaching-reducing agent effective to reduce leaching of the complexed metal biocide from a biodegradable substrate impregnated with the composition relative to an otherwise identical composition lacking the substantially nonionic leaching-reducing agent.

24. A method of making a preservative composition, comprising the steps of:
   a) providing a homogeneous solution comprising a complexed metal biocide derived from ingredients comprising a metal biocide and a complexing agent, wherein the complexing agent and the metal biocide have a complex stability constant $K_1$ in the range from 2.5 to 6.5;
   b) adding a sufficient amount of additional material comprising a metal biocide under conditions effective to form an admixture comprising two phases, wherein a first liquid phase comprises a soluble metal complex biocide and at least an additional portion of the metal biocide is incorporated into a second phase; and c) incorporating at least one water soluble, substantially nonionic leaching-reducing agent into the composition, said water soluble, substantially nonionic leaching-reducing agent having a molecular weight of at least 100 and having a vapor pressure less than that of water at 25° C., said composition including an amount of the substantially nonionic leaching-reducing agent effective to reduce leaching of the complexed metal biocide from a biodegradable substrate impregnated with the composition relative to an otherwise identical composition lacking the substantially nonionic leaching-reducing agent.

25. A method of making a preservative composition, comprising the steps of:
  a) providing a heterogeneous composition comprising a metal biocide in a solid phase;
  b) causing a stoichiometric deficiency of a complexing agent relative to the metal biocide to be present in the composition under conditions to yield two phases, wherein a first liquid phase comprises a soluble metal complex biocide and at least an additional portion of the metal biocide is incorporated into a second phase, wherein the complexing agent and the metal biocide have a complex stability constant $K_1$ in the range from 2.5 to 6.5; and
  c) incorporating at least one water soluble, substantially nonionic leaching-reducing agent into the composition, said water soluble, substantially nonionic leaching-reducing agent having a molecular weight of at least 100 and having a vapor pressure less than that of water at 25° C., said composition including an amount of the substantially nonionic leaching-reducing agent effective to reduce leaching of the complexed metal biocide from a biodegradable substrate impregnated with the composition relative to an otherwise identical composition lacking the substantially nonionic leaching-reducing agent.

26. A method of making a preservative composition, comprising the steps of:
  a) providing a heterogeneous composition comprising a metal biocide in a solid phase;
  b) providing a homogeneous solution comprising a soluble metal complex;
  c) combining amounts of the heterogeneous composition and the homogeneous solution to form an admixture such that the admixture includes a solid phase comprising metal biocide and a liquid phase comprising a soluble metal complex biocide, said phases being in equilibrium, and wherein the complexing agent and the metal biocide have a complex stability constant $K_1$ in the range from 2.5 to 6.5; and
  d) incorporating at least one water soluble, substantially nonionic leaching-reducing agent into the composition, said water soluble, substantially nonionic leaching-reducing agent having a molecular weight of at least 100 and having a vapor pressure less than that of water at 25° C., said composition including an amount of the substantially nonionic leaching-reducing agent effective to reduce leaching of the complexed metal biocide from a biodegradable substrate impregnated with the composition relative to an otherwise identical composition lacking the substantially nonionic leaching-reducing agent.

27. A method of preserving a biodegradable substrate, comprising the step of causing a preservative composition prepared in accordance with claim 1 to contact the substrate.

28. A method of preserving a biodegradable substrate, comprising the step of causing a preservative composition of claim 1 to contact the substrate.

* * * * *